United States Patent
Creaven et al.

(10) Patent No.: US 7,797,987 B2
(45) Date of Patent: Sep. 21, 2010

(54) TEST SENSOR WITH A SIDE VENT AND METHOD OF MAKING THE SAME

(75) Inventors: John P. Creaven, Granger, IN (US); Michael P. VanSickle, Mishawaka, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 254 days.

(21) Appl. No.: 11/973,563

(22) Filed: Oct. 9, 2007

(65) Prior Publication Data

US 2008/0087075 A1 Apr. 17, 2008

Related U.S. Application Data

(60) Provisional application No. 60/850,899, filed on Oct. 11, 2006.

(51) Int. Cl.
*G01N 33/00* (2006.01)
(52) U.S. Cl. .................................................. 73/61.41
(58) Field of Classification Search ................. 73/61.41
See application file for complete search history.

(56) References Cited

U.S. PATENT DOCUMENTS

| | | | |
|---|---|---|---|
| 5,120,420 A | 6/1992 | Nankai et al. | 204/403 |
| 5,194,393 A | 3/1993 | Hugl et al. | 436/525 |
| 5,320,732 A | 6/1994 | Nankai et al. | 204/403 |
| 5,336,388 A | 8/1994 | Leader et al. | 204/406 |
| 5,437,999 A | 8/1995 | Diebold et al. | 435/288 |
| 5,460,968 A | 10/1995 | Yoshida et al. | 436/46 |
| 5,518,689 A | 5/1996 | Dosmann et al. | 422/82.05 |
| 5,582,697 A | 12/1996 | Ikeda et al. | 204/403 |
| 5,611,999 A | 3/1997 | Dosmann et al. | 422/82.05 |
| 5,628,890 A | 5/1997 | Carter et al. | 204/403 |
| 5,660,791 A | 8/1997 | Brenneman et al. | 422/58 |
| 5,676,811 A | 10/1997 | Makino et al. | 204/425 |
| 5,755,953 A | 5/1998 | Henning et al. | 205/778 |

(Continued)

FOREIGN PATENT DOCUMENTS

DE 69208419 T 9/1996

(Continued)

OTHER PUBLICATIONS

European Search Report corresponding to co-pending European patent Application Serial No. 07019769.4-2204, European Patent Office, dated Jan. 29, 2008, 7 pages.

*Primary Examiner*—Hezron Williams
*Assistant Examiner*—Rodney T Frank
(74) *Attorney, Agent, or Firm*—Nixon Peabody LLP

(57) ABSTRACT

A test sensor assisting in determining an analyte concentration in a fluid sample comprises a lid, a base and a spacer. The spacer has first and second spacer sections. The first spacer section has a first spacer side and a first spacer end. The second spacer section has a second spacer side and a second spacer end. The lid, base and spacer are attached such that a fluid chamber is formed between a portion of a lower lid surface and an upper base surface, and between the first and second spacer sides. The lower lid surface, the upper base surface, the first spacer end and the second spacer end form a side vent therebetween that is in communication with the fluid chamber.

34 Claims, 13 Drawing Sheets

U.S. PATENT DOCUMENTS

| | | | |
|---|---|---|---|
| 5,759,364 A | 6/1998 | Charlton et al. | 204/403 |
| 5,798,031 A | 8/1998 | Charlton et al. | 204/403 |
| 5,846,392 A | 12/1998 | Knoll | 204/403 |
| 5,866,349 A | 2/1999 | Lilja et al. | 435/13 |
| 5,997,817 A | 12/1999 | Crismore et al. | 422/58 |
| 6,004,441 A | 12/1999 | Fujiwara et al. | 204/412 |
| 6,036,919 A | 3/2000 | Thym et al. | 422/58 |
| 6,129,823 A | 10/2000 | Hughes et al. | 204/409 |
| 6,143,164 A | 11/2000 | Heller et al. | 205/777.5 |
| 6,254,736 B1 | 7/2001 | Earl et al. | 204/164 |
| 6,270,637 B1 | 8/2001 | Crismore et al. | 204/403 |
| 6,531,040 B2 | 3/2003 | Musho et al. | 204/401 |
| 6,540,891 B1 | 4/2003 | Stewart et al. | 204/403.14 |
| 6,841,052 B2 | 1/2005 | Musho et al. | 204/401 |
| 7,122,102 B2 | 10/2006 | Wogoman | 204/400 |
| 7,125,481 B2 | 10/2006 | Musho et al. | 205/775 |
| 7,138,041 B2 | 11/2006 | Su et al. | 204/403.04 |
| 2004/0007461 A1 | 1/2004 | Edelbrock et al. | 204/403.11 |
| 2004/0194302 A1 | 10/2004 | Bhullar et al. | 29/847 |
| 2004/0214345 A1 | 10/2004 | Matzinger et al. | 436/514 |
| 2004/0253367 A1 | 12/2004 | Wogoman | 427/58 |
| 2005/0013731 A1* | 1/2005 | Burke et al. | 422/56 |
| 2005/0016844 A1* | 1/2005 | Burke et al. | 204/403.01 |
| 2005/0183953 A1 | 8/2005 | Su et al. | 204/403.01 |
| 2005/0224345 A1 | 10/2005 | Taniike et al. | 204/403.01 |
| 2006/0070878 A1 | 4/2006 | Wu et al. | 204/403.01 |
| 2009/0078030 A1* | 3/2009 | Jung | 73/61.41 |

FOREIGN PATENT DOCUMENTS

| | | |
|---|---|---|
| EP | 0 537 761 A2 | 4/1993 |
| EP | 0 538 830 A1 | 4/1993 |
| EP | 1 360 932 A1 | 11/2003 |
| EP | 1 413 879 A1 | 4/2004 |
| JP | 5-126745 | 5/1993 |
| JP | 5-256811 | 10/1993 |
| WO | WO 03/005015 A1 | 1/2003 |
| WO | WO 03/012421 A1 | 2/2003 |
| WO | WO 2005/078436 A1 | 8/2005 |

* cited by examiner

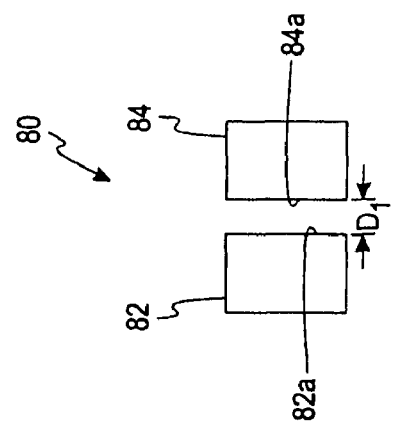
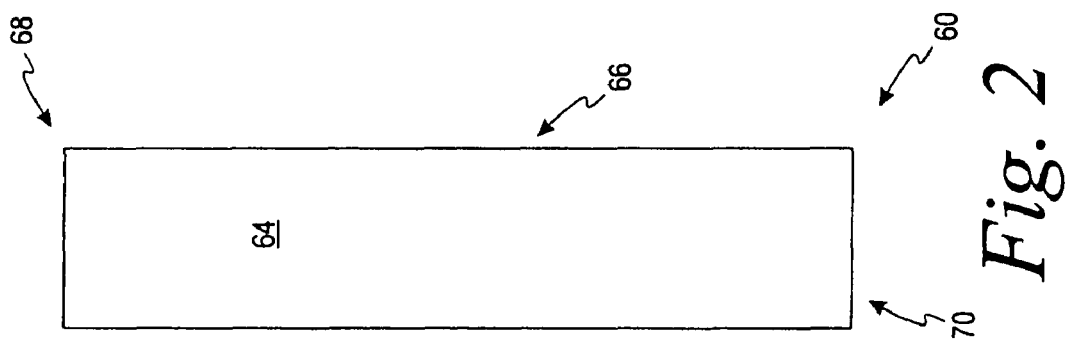
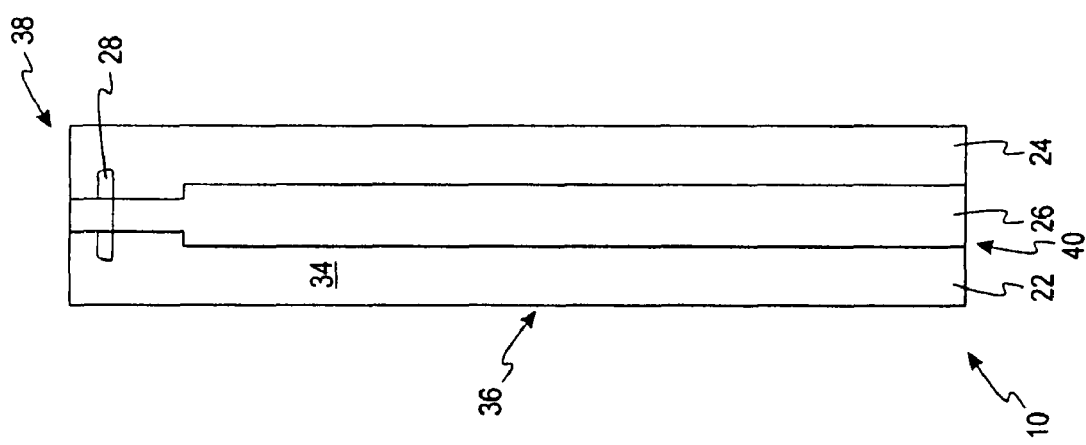

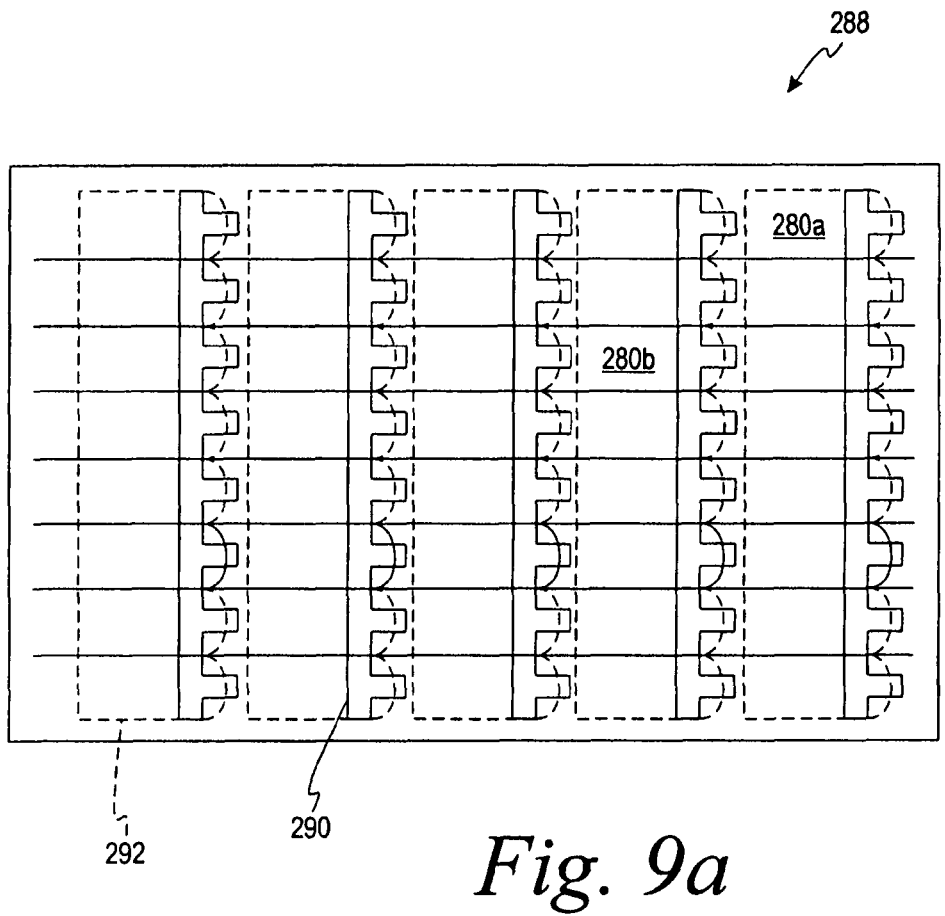
*Fig. 9a*
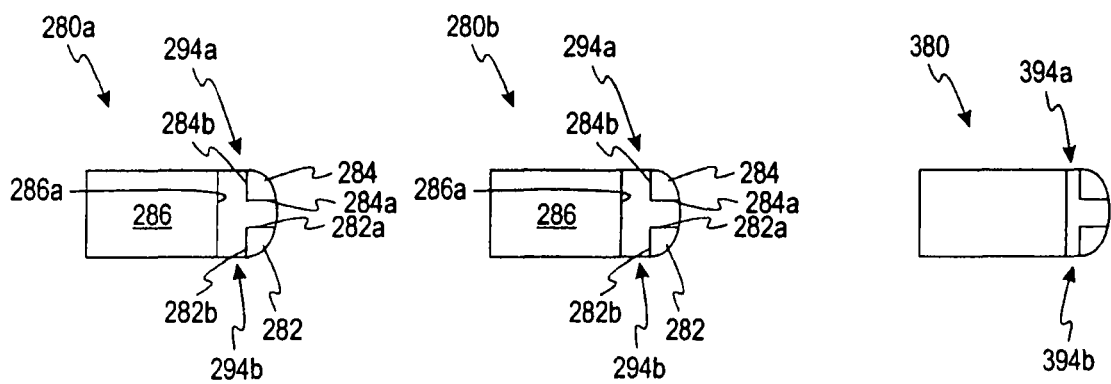
*Fig. 9b*  *Fig. 9c*  *Fig. 10*

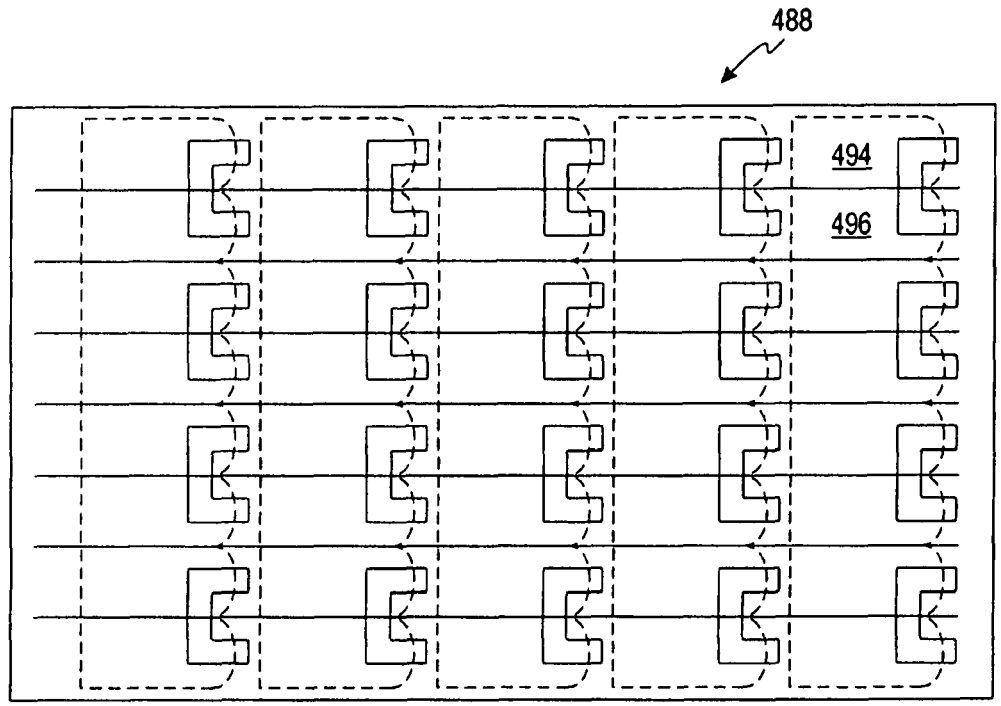
*Fig. 11a*
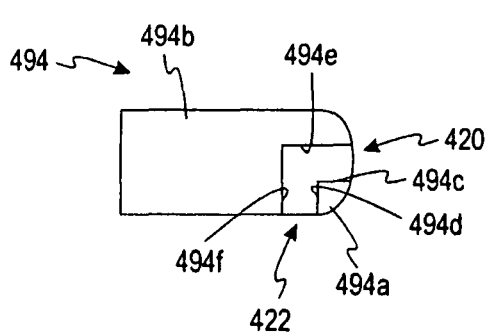 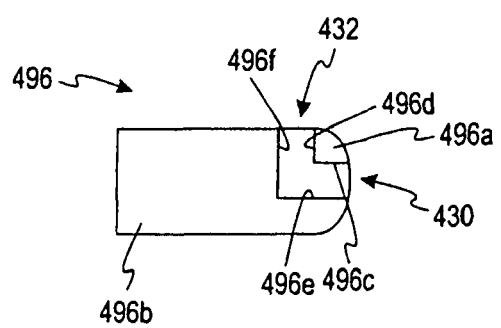
*Fig. 11b*  *Fig. 11c*
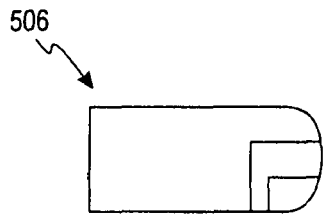 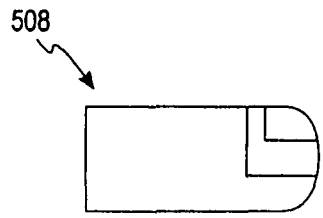
*Fig. 12a*  *Fig. 12b*

TEST SENSOR WITH A SIDE VENT AND METHOD OF MAKING THE SAME

CROSS-REFERENCE TO RELATED APPLICATIONS

This application claims priority to U.S. Provisional Application Ser. No. 60/850,899 filed on Oct. 11, 2006, which is incorporated by reference in its entirety.

FIELD OF THE INVENTION

The present invention generally relates to a test sensor. More specifically, the present invention generally relates to a test sensor with a side vent to assist in the capillary flow of fluid.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

The test sensor is adapted to receive fluid (e.g., blood) from a user. The test sensor typically includes a base and a lid that is attached to the base. Existing test sensors differ in the manner in which they receive fluids. In one existing test sensor, a channel is formed between a generally U-shaped spacer and is adapted to receive blood from a user. A user then places blood from, for example, his/her finger into the channel. Some test sensors receive blood via capillary action. In test sensors that receive fluid (e.g., blood) using capillary action, the test sensor needs at least one vent at an opposing end of the capillary channel from the blood-entry opening for the blood to flow into the capillary channel. One existing method of forming a vent includes creating an aperture in the lid or the base of the test sensor. Another existing method of forming a vent includes incorporating a mesh into a lid, which in effect creates a breathable surface or a vent in the lid. Such existing methods include additional processing steps that increase the manufacturing cost of a test sensor.

Therefore, it would be desirable to have a test sensor that provides at least one vent that can be manufactured in a more cost-effective and/or efficient manner.

SUMMARY OF THE INVENTION

In one embodiment, a test sensor is adapted to assist in determining the concentration of an analyte in a fluid sample. The test sensor comprises a lid, base and a spacer. The lid has an upper lid surface and a lower lid surface. The base has an upper base surface and a lower base surface. The spacer has at least a first spacer section and a second spacer section. The first spacer section has a first spacer side and a first spacer end. The second spacer section has a second spacer side and a second spacer end. The lid, base and spacer are attached such that a fluid chamber is formed between a portion of the lower lid surface and the upper base surface, and between the first and second spacer sides. The lower lid surface, the upper base surface, the first spacer end and the second spacer end form at least one side vent therebetween. The at least one vent is in communication with the fluid chamber.

In one method, an analyte concentration of a fluid sample is determined using a meter. The method comprises providing a test sensor having a lid, a base and a spacer. The lid has an upper lid surface and a lower lid surface. The base has an upper base surface and a lower base surface. The spacer has at least a first spacer section and a second spacer section. The first spacer section has a first spacer side and a first spacer end. The second spacer section has a second spacer side and a second spacer end. The lower lid surface, upper base surface, the first spacer end and the second spacer end form at least one side vent therebetween. The fluid sample is placed in the fluid chamber between the lower lid surface, the upper base surface, first spacer side, and the second spacer side. The fluid chamber is in communication with the at least one vent. The analyte concentration of the sample is determined using the test sensor and the meter.

According to another method, a test sensor is formed that is adapted to assist in determining an analyte concentration of a fluid sample. The method comprises providing a lid having an upper lid surface and a lower lid surface. A base is provided having an upper base surface and a lower base surface. A spacer is provided having at least a first spacer section and a second spacer section. The first spacer section has a first spacer side and a first spacer end. The second spacer section has a second spacer side and a second spacer end. The lid, base and the spacer are attached such that a fluid chamber is formed between a portion of the lower lid surface and the upper base surface, and between the first and second spacer sides. At least one side vent is formed between the first spacer end, the second spacer end, the lower lid surface and the upper base surface. The at least one vent is in communication with the fluid chamber.

According to a further method, a test sensor is formed that is adapted to assist in determining an analyte concentration of a fluid sample. The method comprises providing a lid sheet having an upper lid surface and a lower lid surface. A base sheet is provided having an upper base surface and a lower base surface. A spacer sheet is provided having a first spacer section and a second spacer section. The first spacer section includes a first spacer side and a first spacer end. The second spacer section includes a second spacer side and a second spacer end. Material is removed from the spacer sheet that will assist in forming at least one vent and a fluid chamber. The lid sheet, base sheet and the spacer sheet are attached such that the fluid chamber and at least one vent are formed. The fluid chamber is formed between the lower lid surface, the upper base surface, the first spacer side and the second spacer side. The at least one vent is formed between the first spacer end, the second spacer end, the lower lid surface and the upper base surface. The at least one vent is in communication with the fluid chamber. A plurality of test sensors is formed from the attached lid sheet, base sheet and spacer sheet.

BRIEF DESCRIPTION OF THE DRAWINGS

FIG. 1 is a top view of a base to be used in forming a test sensor according to one embodiment.

FIG. 2 is a top view of a lid to be used in forming a test sensor according to one embodiment.

FIG. 3 is a top view of a spacer to be used in forming a test sensor according to one embodiment.

FIG. 9*a* is a top view of a spacer sheet according to one embodiment.

FIG. 9*b* is a top view of one of the sensor spacers from the spacer sheet of FIG. 9*a*.

FIG. 9*c* is a top view of another one of the sensor spacers from the spacer sheet of FIG. 9*a*

FIG. 10 is a spacer to be used in forming a test sensor according to another embodiment.

FIG. 11*a* is a top view of a spacer sheet according to another embodiment.

FIG. 11*b* is an enlarged view of one of the sensor spacers from the spacer sheet of FIG. 11*a*.

FIG. 11*c* is an enlarged view of another one of the sensor spacers from the spacer sheet of FIG. 11*a*

FIGS. 12*a*, 12*b* are sensor spacers to be used in forming a test sensor according to other embodiments.

DETAILED DESCRIPTION OF ILLUSTRATED EMBODIMENTS

The present invention is directed to an improved test sensor that is adapted to assist in determining the analyte concentration in a fluid. In one embodiment, a test sensor is adapted to receive a fluid sample and is analyzed using an instrument or meter. Analytes that may be measured include glucose, lipid profiles (e.g., cholesterol, triglycerides, LDL and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

The test sensors include at least a base, a lid and a spacer. The base, lid and spacer may be made from a variety of materials such as polymeric materials. Non-limiting examples of polymeric materials that may be used to form the base, lid and spacer include polycarbonate, polyethylene terephthalate (PET), polyethylene naphthalate (PEN), polyimide and combinations thereof.

Figure 4A:
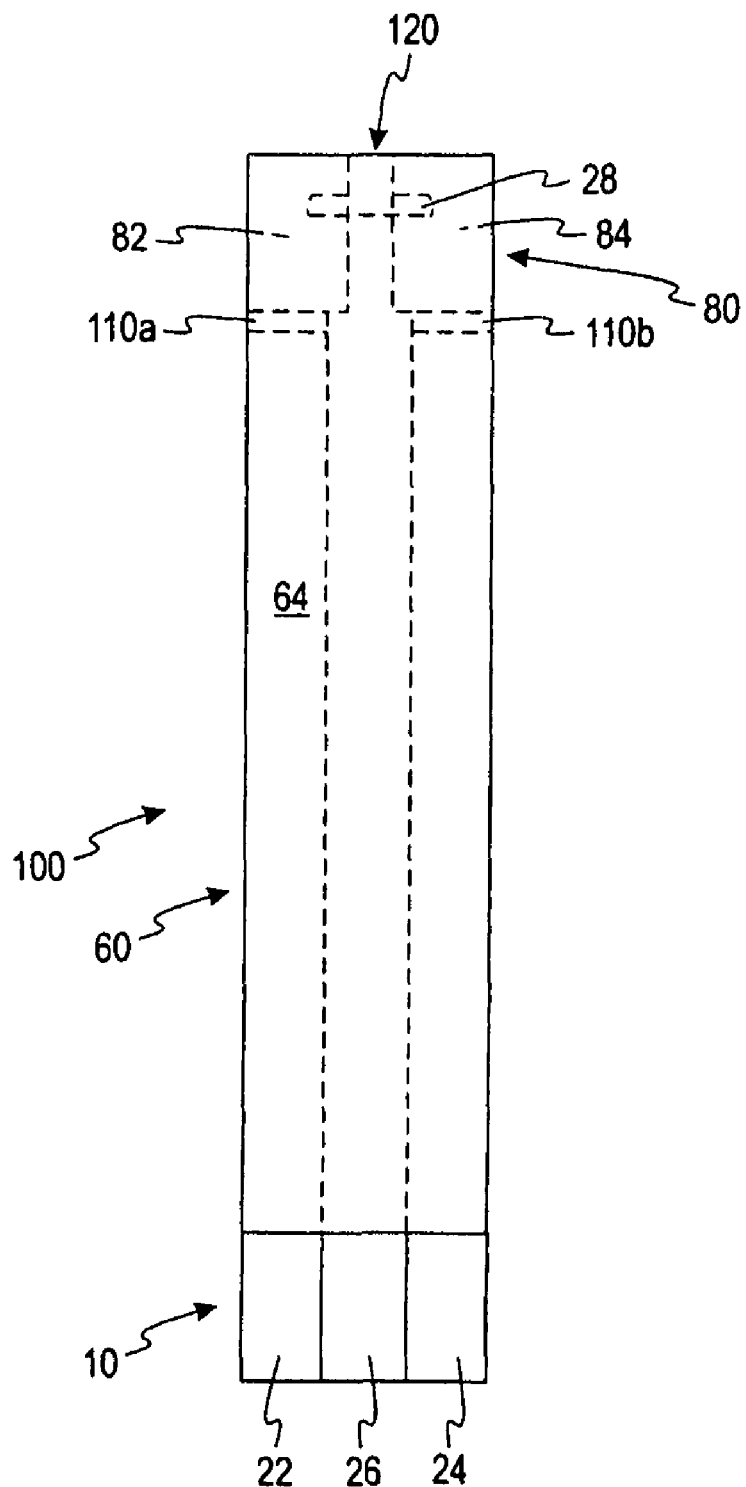
FIG. 4*a* is a top view of an electrochemical test sensor using the base of FIG. 1, the lid of FIG. 2 and the spacer of FIG. 3.
Figure 4B:
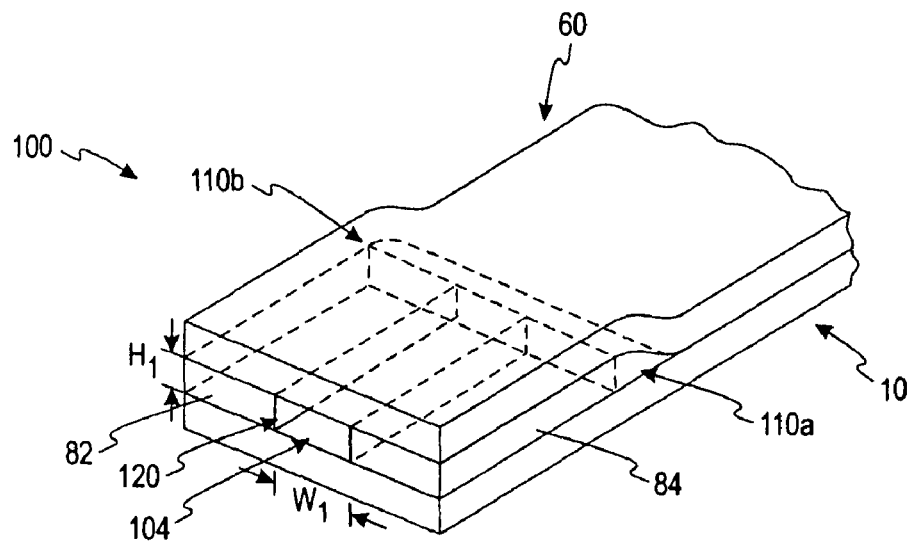
FIG. 4*b* is a partial perspective view of the test sensor of FIG. 4*a*.
Figure 4C:
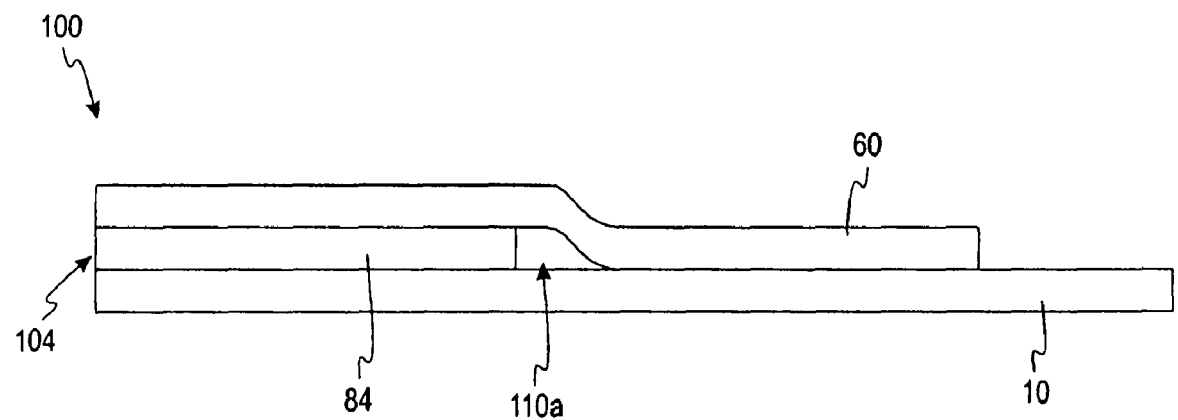
FIG. 4*c* is a side view of the test sensor of FIG. 4*a*.

In one embodiment, the test sensor is an electrochemical test sensor. One non-limiting example of a test sensor (test sensor 100) is shown in FIGS. 4*a*-4*c*. The test sensor 100 of FIGS. 4*a-c* is formed using a base 10 of FIG. 1, a lid 60 of FIG. 2 and a spacer 80 of FIG. 3. When the base 10, the lid 60 and the spacer 80 are attached together, a fluid chamber 120 (FIG. 4*b*) is formed. The fluid chamber 120 provides a flow path for introducing the sample into the test sensor 100 and eventually contacting the electrodes, as will be discussed below. The fluid chamber 120 also extends through to at least one vent, as will be discussed below.

Referring back to FIG. 1, the base 10 includes a plurality of electrodes 22, 24, 26 and a fluid-receiving area 28 that contains an enzyme. The enzyme is selected to react with the desired analyte or analytes to be tested so as to assist in determining an analyte concentration of a fluid sample. The fluid-receiving area 28 includes a reagent for converting an analyte of interest (e.g., glucose) in a fluid-test sample (e.g., blood) into a chemical species that is electrochemically measurable, in terms of the electrical current it produces, by the components of the electrode pattern. The reagent typically contains an enzyme such as, for example, glucose oxidase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. If the concentration of another analyte is to be determined, an appropriate enzyme is selected to react with the analyte.

The fluid-receiving area 28 may comprise a polymer, an enzyme, and an electron acceptor. The fluid-receiving area 28 may further include a mediator that is an electron acceptor and assists in generating a current that corresponds to the analyte concentration. If the enzyme is glucose oxidase, then a mediator (e.g., potassium ferricyanide) may be included. The fluid-receiving area 28 also may include additional ingredients such as a buffer and a surfactant in some embodiments.

The plurality of electrodes of FIG. 1 includes counter electrodes 22, 24 and a working electrode 26 in this embodiment. In one embodiment, an analyte concentration is only reported if the tested fluid contacts both of the counter electrodes and, thus, the test sensor in this embodiment has underfill protection. In another embodiment, the plurality of electrodes includes one counter electrode and two working electrodes. In this embodiment, the analyte concentration of one working electrode should be the same or generally correspond to the other analyte concentration of the other working electrodes to ensure that the sample size is sufficient. Thus, this embodiment also has underfill protection.

It is contemplated that more or less electrodes may be formed in the base that is used in forming the electrochemical test sensor. For example, in other embodiments, the test sensor may include exactly two electrodes or at least four electrodes. The exactly two electrodes may be a working and counter electrode in which an electrochemically created current flows when these electrodes are electrically connected and potential created between them.

The flow of electrons created by the enzymatic reaction flows through the working electrode to a meter that measures the magnitude of the current flow. The counter electrode provides a fixed potential against which the working electrode is controlled. The counter electrode may also be used to complete the electrical circuit. The test sensor may include a detection electrode that detects an underfill condition. It is contemplated that other electrodes may be used such as a hematocrit electrode that assists in correcting for the bias that occurs with selected hematocrit concentrations.

The electrodes may be formed on the base by a variety of methods such as, for example, printing onto the base. The electrodes are formed of conductive materials such as, for example, metallic materials (e.g., gold, platinum, palladium, rhodium, ruthenium, or combinations thereof) or carbon.

The electrodes may be defined by a laser to cut the pattern or may be defined by using a mask. For example, the plurality of electrodes 22, 24, 26 may be defined by using a mask and a laser such as, for example, an Excimer laser or a carbon dioxide-based laser. One example of a mask is a chrome-on-glass mask in which the beam of light is only allowed to pass through selected areas. According to another method, the plurality of electrodes may be defined with a laser using direct writing of the lines. In this method, the laser beam of light is moved so as to define the plurality of electrodes. Lasers that produce a beam of energy capable of removing a layer and that can be moved to form a pattern may be used in this method. Non-limiting examples of such lasers are carbon dioxide-based lasers and yttrium-based lasers such as yttrium aluminum garnet (YAG) lasers.

It is contemplated that the plurality of electrodes may be defined by other methods such as, for example, printing (e.g., screen-printing), coating (e.g., reverse roll), vapor deposition, sputtering, and electrochemical deposition.

The base 10 of FIG. 1 includes an upper base surface 34 and a lower base surface 36. The base 10 includes a first base end 38 and a second base end 40, in which the first base end 38 and the second base end 40 are located on opposing ends of the base 10. Similarly, the lid 60 of FIG. 2 includes an upper lid surface 64 and a lower lid surface 66. The lid 60 includes a first lid end 68 and a second lid end 70, in which the first lid end 68 and the second lid end 70 are located on opposing ends of the lid 60. The lower lid surface may be treated with surfactant to enhance the sample harvesting.

The spacer 80 of FIG. 3 includes a first spacer section 82 and a second spacer section 84. A distance D1 is formed between a first spacer side 82a of the first spacer section 82 and a second spacer side 84a of the second spacer section 84. The distance D1 will form the width of the fluid chamber of the test sensor. The distance D1 is shown as being generally constant between the first and second spacer sections 82, 84. It is contemplated, however, that the distance between the first and second spacer section may vary.

Examples of components, such as those mentioned above, used in forming electrochemical test sensors, including their operation, may be found in, for example, U.S. Pat. No. 6,531,040 B2.

Figure 5A:
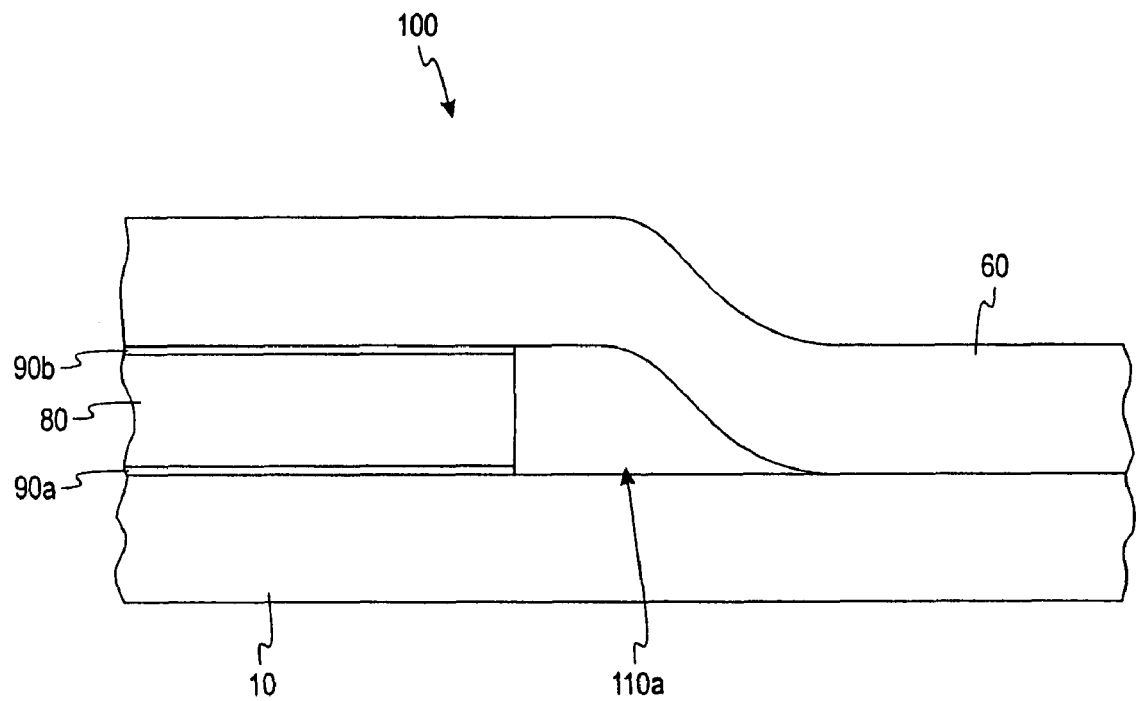
FIG. 5*a* is a partial side view of the test sensor of FIG. 4*a* that includes a base, a lid, a spacer and two adhesive layers according to another embodiment.

To form the test sensor 100 of FIGS. 4a-c, the base 10, the spacer 80, and the lid 60 are attached. In one embodiment shown in FIG. 5a, the base 10 and the spacer 80 are attached via an adhesive 90a and the spacer 80 and the lid 60 are attached via an adhesive 90b. It is contemplated that other materials may be used that have sticking properties such that the lid, base and spacer remain attached.

The base 10 may be laminated to the spacer 80 using, for example, a pressure-sensitive adhesive and/or a hot melt adhesive. Thus, the lamination between the base and the spacer uses pressure, heat or the combination thereof. It is contemplated that other materials may be used to attach the base to the spacer. Similarly, the lid 60 and the spacer 80 may be attached using the same or a different adhesive than the adhesive used between the base 10 and the spacer 80.

It is contemplated that the base and spacer may be attached by other methods such as heat sealing. Similarly, the lid and the spacer may be attached by other methods such as heat sealing. Thus, in this embodiment, the test sensor includes a base, a spacer and a lid without an adhesive layer. For example, the spacer may be made of a lower melting temperature material than the lid and the base. The heat sealing may be accomplished by, for example, sonic welding.

Figure 5B:
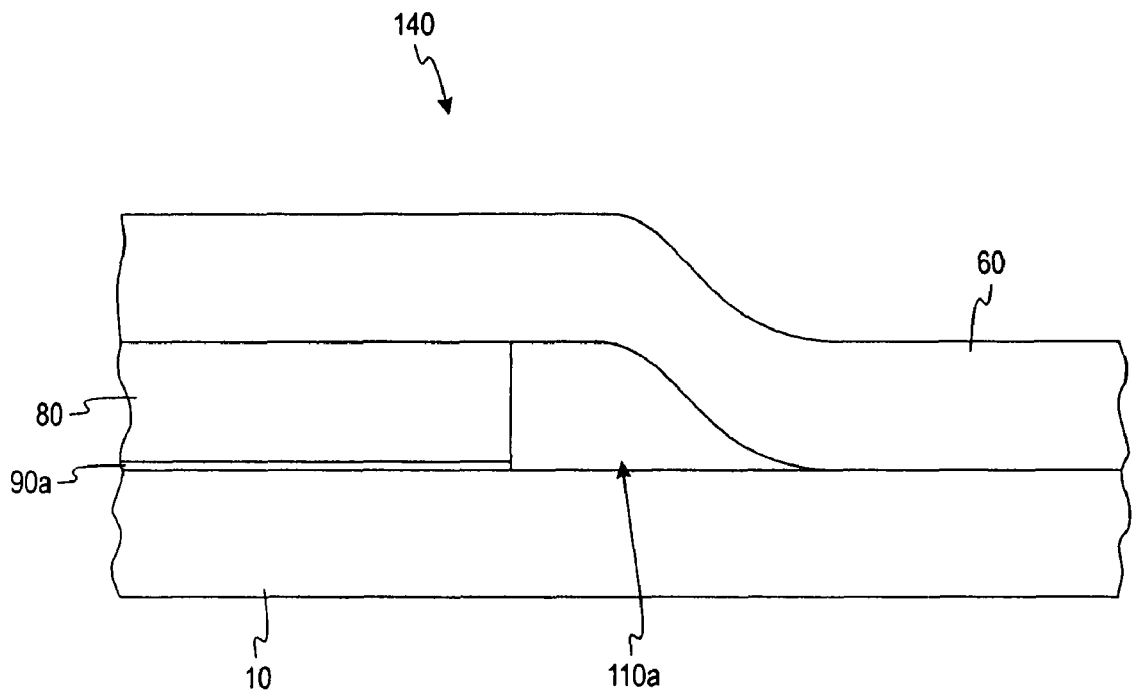
FIG. 5*b* is a partial side view of a test sensor that includes a base, a lid, a spacer and one adhesive layer according to a further embodiment.

In another embodiment, the lid or base may be heat-sealed to the spacer with the remaining one of the lid and base being adhesively attached to the spacer. For example, the lid and spacer may be heat sealed while the base is attached to the spacer via an adhesive layer (see, e.g., test sensor 140 of FIG. 5b).

According to another embodiment, a spacer-lid combination is used in which the spacer and lid have been previously attached before being attached to the base. According to a further embodiment, a spacer-base combination is used in which the spacer and the base have been previously attached before being attached to the lid.

After the base 10, lid 60 and spacer 80 are attached, the fluid chamber 120 is formed between a portion of the lower lid surface 66, the upper base surface 34 and the first and second spacer sides 82a, 84a. The fluid chamber 120 is formed between the lower lid surface 66 and the upper base surface 34 at or near the first lid end 68 and the first base end 38. As shown in FIG. 4b, the fluid chamber 120 is adapted to receive a fluid from a fluid-receiving end 104.

The fluid chamber 120 as shown in FIG. 4b has a height H1 that is generally from about 1 to about 10 mils. More specifically, the fluid chamber 120 as shown in FIG. 4b, has a height H1 that is generally from about 3 to about 7 mils. Similarly, the fluid chamber 120 as shown in FIG. 4b has a width W1 that is generally from about 1 to about 10 mils. More specifically, the fluid chamber 120 as shown in FIG. 4b, has a width W1 that is generally from about 3 to about 7 mils. It is desirable for the height H1 and width W1 to be able to receive the fluid (e.g., blood) from a user while still maintaining the blood within the confines of the fluid chamber 120. It is contemplated that the fluid chamber may be of other shapes and dimensions.

The fluid chamber is in communication with at least one vent. As shown in FIG. 4b, the fluid chamber 120 is in communication with a plurality of vents 110a, 110b. The vents assist in making the fluid (e.g., blood) flow into the fluid chamber 120 of the test sensor via capillary action. In an electrochemical test sensor, the at least one side vent typically is located around or just past the working/counter electrode area.

The vents are formed in one embodiment by laminating the lid, base and spacer in which there is a gap that is intentionally left between the lid, spacer and base. As shown in FIGS. 4, 5, the test sensor 100 is formed with the vents 110a, 110b. The vents 110a, 110b are located on opposing sides of the electrochemical test sensor 100 as shown in FIG. 4b. As shown in FIG. 4b, the vents 110a, 110b are located generally perpendicular to the fluid chamber 120. More specifically, the vents 110*a*, 110*b* are located substantially perpendicular or perpendicular to the fluid chamber 120. It is contemplated that the at least one vent may be located in other directions to the fluid chamber such as generally diagonal with the fluid chamber.

In one method, the electrochemical test sensor is formed by attaching a base sheet with a plurality of electrodes to a spacer sheet, which has been previously punched or cut out. The spacer sheet may be punched using a punch tool or laser cut. The base sheet is typically unpunched or uncut at the time of the attachment to the spacer sheet. The attachment of the base sheet to the spacer sheet may be done by a lamination process. A lid sheet is then attached to the base sheet/spacer sheet using, for example, a step-lamination process. This method is advantageous in that the formed vents do not have to be machined separately (e.g., punched or cut) in the lid or base, which eliminates an extra processing step.

Figure 6A:
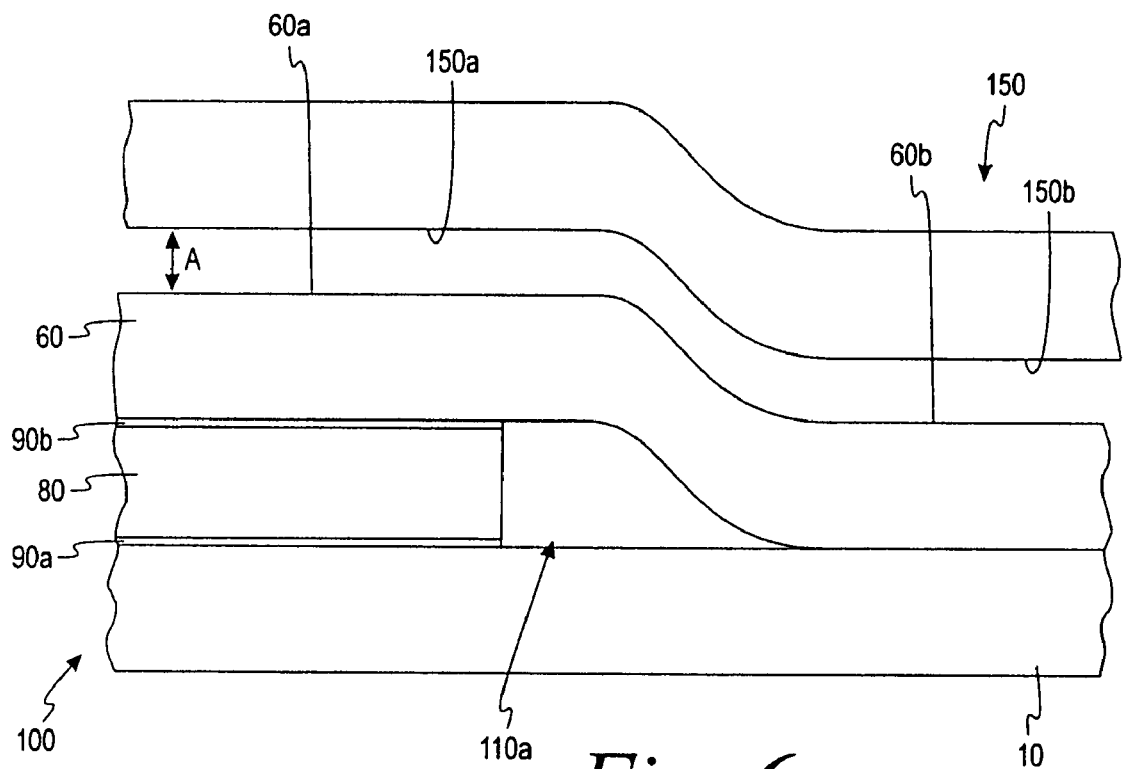
FIG. 6*a* is a partial side view of the test sensor of FIG. 4*a* being formed with a reciprocating platen.

Referring to FIG. 6*a*, in a one step-lamination process, the at least one vent may be formed by using a reciprocating stepped platen 150. The platen 150 moves in a generally vertical direction along arrow A. The stepped platen includes a first contact surface 150*a* and a second contact surface 150*b*. The first contact surface 150*a* contacts lid portion 60*a* that lies above the spacer 80 and the base 10. The second contact surface 150*b* contacts lid portion 60*b* that lies only above the base 10.

Figure 6B:
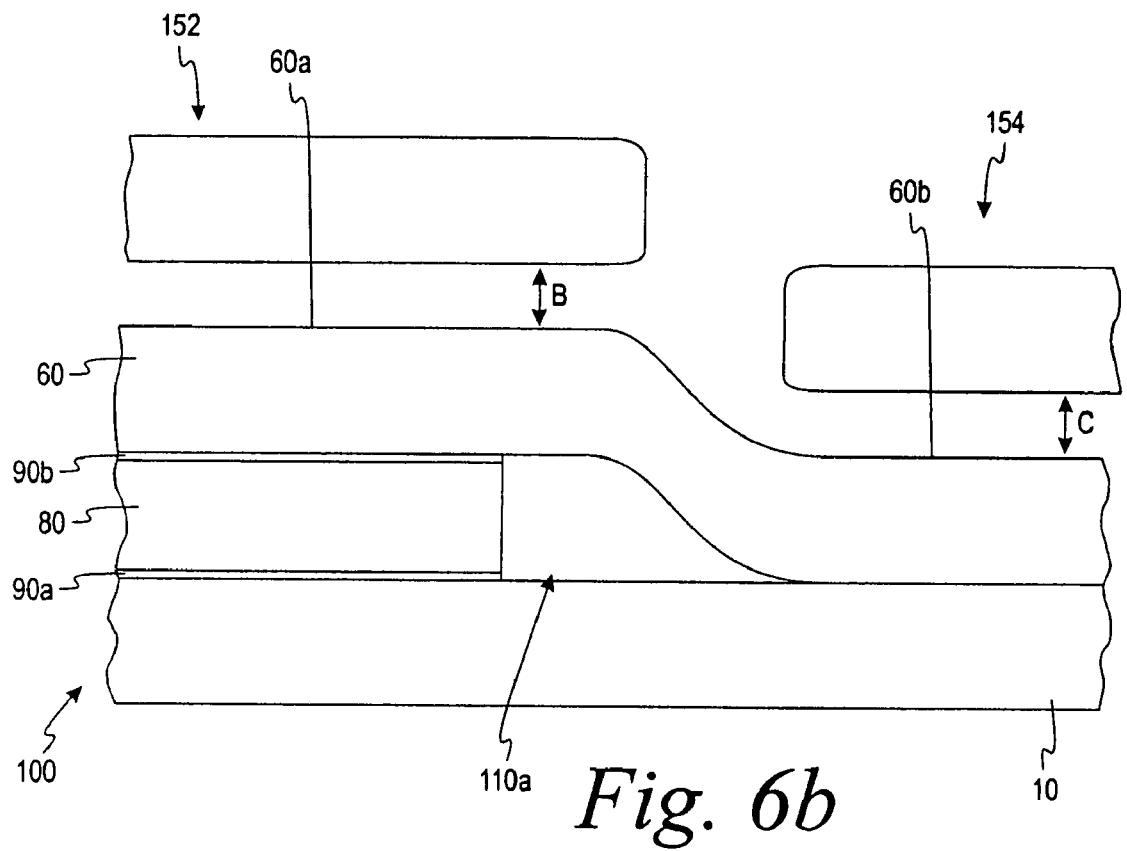
FIG. 6*b* is a partial side view of the test sensor of FIG. 4*a* being formed with a plurality of platens.

Similarly, in FIG. 6*b*, a plurality of platens 152, 154 functions together to form the at least one vent of the test sensor. The platens 152, 154 move in a generally vertical direction along respective arrows B, C. The platen 152 contacts the lid portion 60*a* that lies above the spacer 80 and the base 10. The platen 154 contacts lid portion 60*b* that lies only above the base 10. It is contemplated that the vents of the test sensor may be formed with other apparatus than that shown in FIGS. 6*a*, 6*b*.

In another method, as will be discussed in more detail with respect to FIGS. 7 and 13, the electrochemical test sensor is formed by attaching a lid sheet to a spacer sheet, which has been previously punched or cut out. The spacer sheet may be punched using a punch tool or laser cut. The lid sheet is typically unpunched or uncut at the time of the attachment to the spacer sheet. The attachment of the lid sheet to the spacer sheet may be done by a lamination process. This method of first attaching the lid and the spacer may be advantageous because it reduces or limits the reagent exposure on the base to temperature in multiple lamination steps in a hot melt adhesive application.

A base sheet with a plurality of electrodes is then laminated to the attached lid sheet/spacer sheet using a step-lamination process. This method is advantageous in that the vents that are formed do not have to be machined separately (e.g., punched or laser cut) in the sensor lid or base, which eliminates an extra processing step.

Figure 7A:
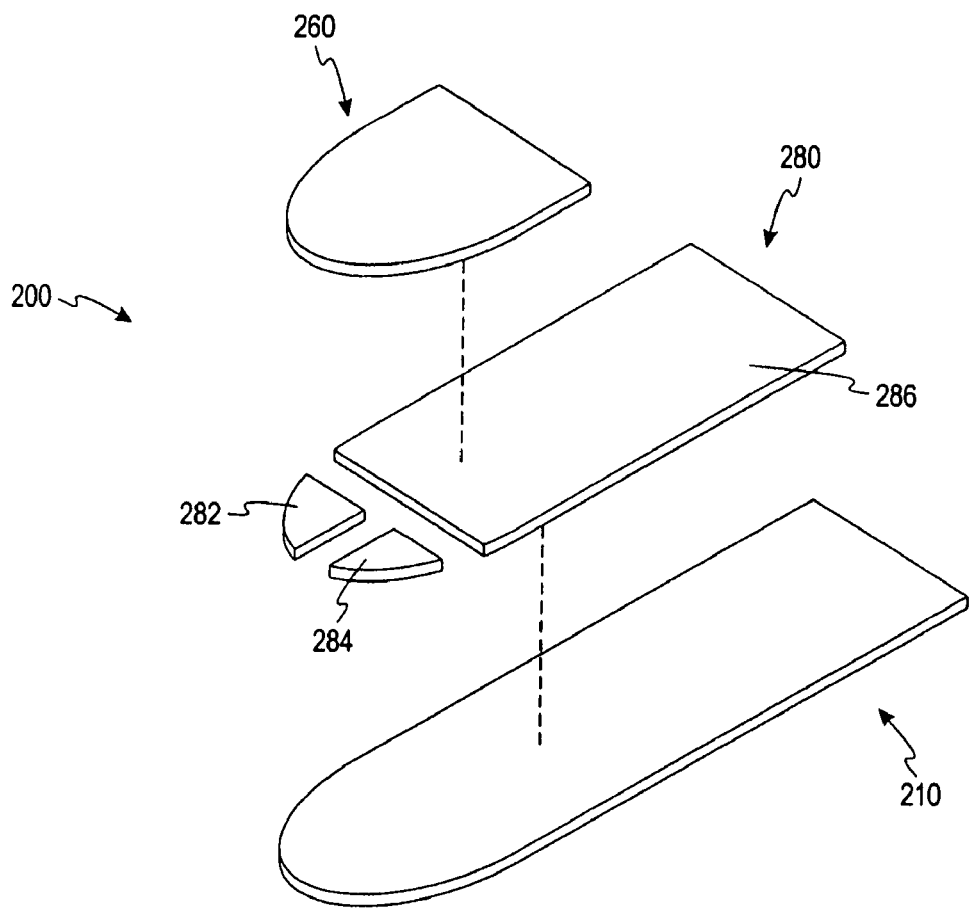
FIG. 7*a* is an exploded perspective view of an electrochemical test sensor according to another embodiment.
Figure 7B:
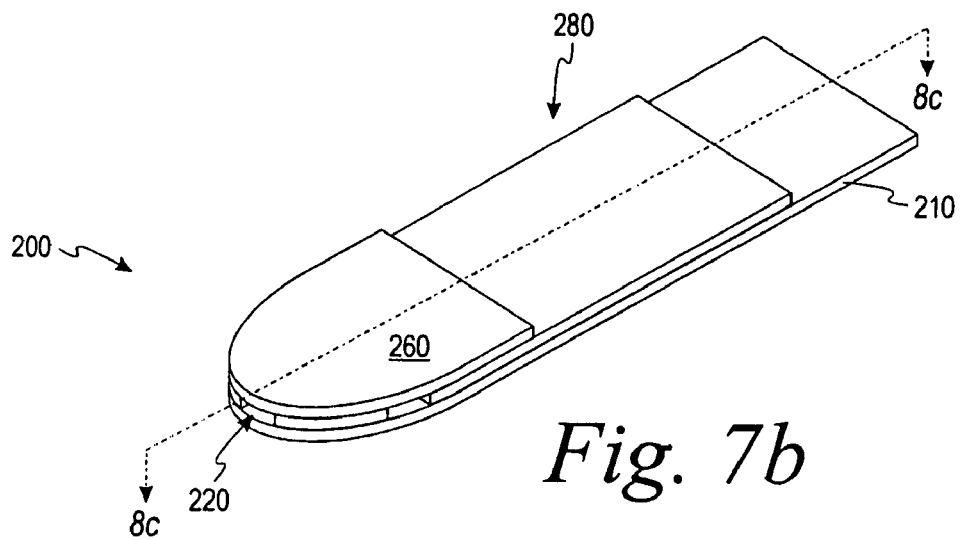
FIG. 7*b* is an assembled perspective view of the test sensor of FIG. 7*a*.
Figure 8A:
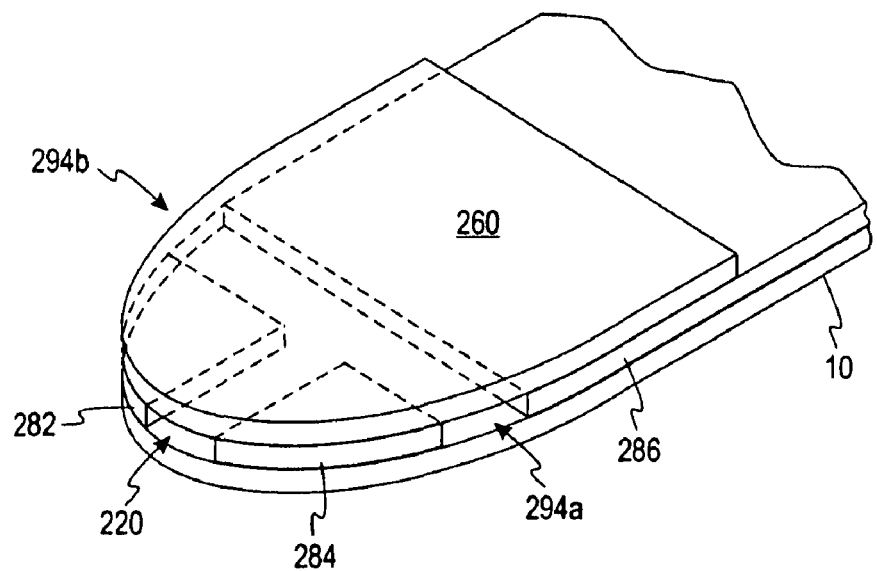
FIG. 8*a* is a partial enlarged perspective view of the test sensor of FIG. 7*b*.
Figure 8B:
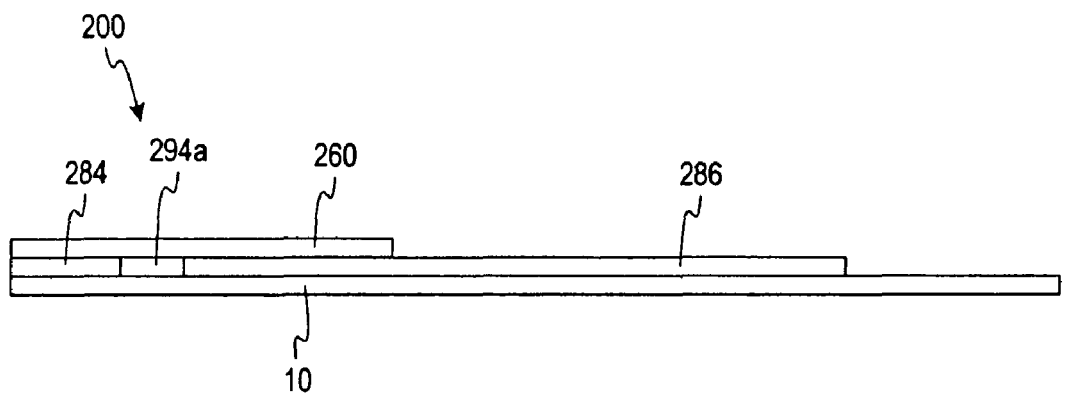
FIG. 8*b* is a side view of the test sensor of FIG. 7*b*.
Figure 8C:
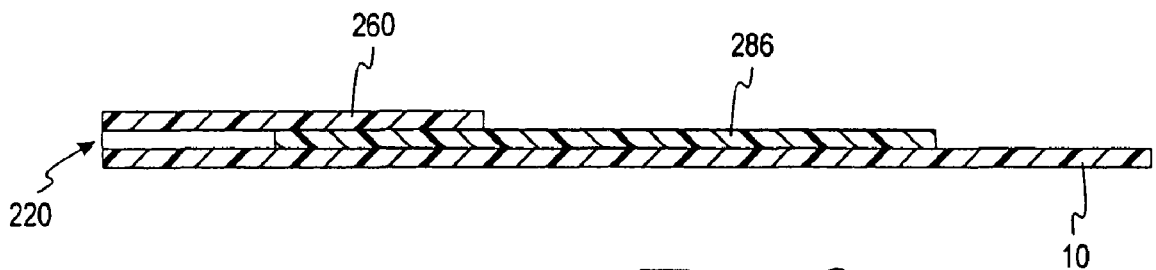
FIG. 8*c* is a cross-sectional view taken generally along line 8*c*-8*c* of FIG. 7*b*.

In a further method, the at least one vent may be formed by first punching or cutting a spacer sheet to create a space that will eventually assist in forming the fluid chamber and the at least one vent. Referring to FIG. 7*a*, an exploded view of an electrochemical test sensor 200 is shown that includes a base 210, a lid 260 and a spacer 280. The base 210 may include the features that are described above with respect to base 10. The spacer 280 includes a first spacer section 282, a second spacer section 284 and a third spacer section 286. The first and second spacer sections 282, 284 assist in defining the fluid chamber 220 (see FIGS. 7*b*, 8*a*, 8*c*).

The spacer 280 to be used in the test sensor 200 may be formed from a spacer sheet. One example of a spacer sheet is shown in FIG. 9*a* with spacer sheet 288. The spacer sheet 288 is adapted to form a plurality of spacers. In one method, the spacer sheet 288 is punched or cut out in a first operating act generally along a plurality of solid punching lines 290. Then the spacer sheet 288 is later punched or cut again in a second operating act along dashed lines 292 that forms the final shape of the spacer to be used in the test sensor. The result of the first and second punching and/cut out acts is a plurality of spacers 280.

The spacers 280 *a,b* of FIGS. 9*b*, 9*c* are shown from two respective enlarged areas of the spacer sheet 288 in FIG. 9*a*. The spacer 280*a*, for example, includes the first spacer section 282, the second spacer section 284 and the third spacer section 286. The first spacer section 282 includes a side 282*a* and an end 282*b*. The second spacer section 284 includes a side 284*a* and an end 284*b*. The third spacer section 286 includes an end 286*a*. The sides 282*a*, 284*a* assist in forming the fluid chamber. The ends 282*b*, 284*b* and 286*b* assist in forming a plurality of vents 294*a*, 294*b*.

In one method, the second operating act along dashed lines 292 in the spacer sheet 288 is not performed until the lid sheet, spacer sheet 288 and the base sheet are already attached to each other. The lid, spacer and the base sheets in this embodiment may be attached by methods such as, for example, via an adhesive (e.g., a pressure-sensitive adhesive and/or a hot melt adhesive), lamination, heat-sealing and combinations thereof. Since in this embodiment the attachment of the lid, spacer and base sheets are attached before forming the individual test sensors, tight process control of the fluid chamber may be achieved. This may be achieved in one method because the spacer-punch tool or cutting tool (e.g., laser) can accurately define the spacer, which assists in forming the capillary channel.

It is contemplated that the spacer may be shaped differently such as, for example shown in FIG. 10. FIG. 10 depicts a spacer 380 that is similar to the spacers 280*a, b*, except that the width of the vents 394*a*, 394*b* are more narrow than the width of the vents 294*a*, 294*b*. By having the width of the vents more narrow, this will typically assist in maintaining the integrity of the spacer sheet after punching or cutting.

Referring to FIG. 11*a-c*, a spacer sheet according to another embodiment is shown. A spacer sheet 488 is adapted to produce a plurality of spacers that includes exactly one vent. As shown in FIGS. 11*b*, 11*c*, spacers 494, 496 have been punched or cut from the spacer sheet 488 at selected locations. Each of the spacers 494, 496 is adapted to form exactly one side vent. As shown in FIGS. 11*b*, 11*c*, the vents 422, 432 are located on opposing sides of the test sensor.

Specifically, spacer 494 of FIG. 11*b* includes a first spacer section 494*a* and a second spacer section 494*b*. The first spacer section 494*a* includes a side 494*c* and an end 494*d*. The second spacer section 494*b* includes a side 494*e* and an end 494*f*. The sides 494*c*, 494*e* assist in forming a fluid chamber 420. The ends 494*d*, 494*f* assist in forming the vent 422.

Similarly, spacer 496 of FIG. 11*c* includes a first spacer section 496*a* and a second spacer section 496*b*. The first spacer section 496*a* includes a side 496*c* and an end 496*d*. The second spacer section 496*b* includes a side 496*e* and an end 496*f*. The sides 496*c*, 496*e* assist in forming fluid chamber 430. The ends 496*d*, 496*f* assist in forming the vent 432.

It is contemplated that other vent sizes may be used than shown in FIGS. 11*b, c*. An example of a spacer with exactly one side vent is shown with a reduced width with spacers 506, 508 of respective FIGS. 12*a*, 12*b*.

Figure 13A:
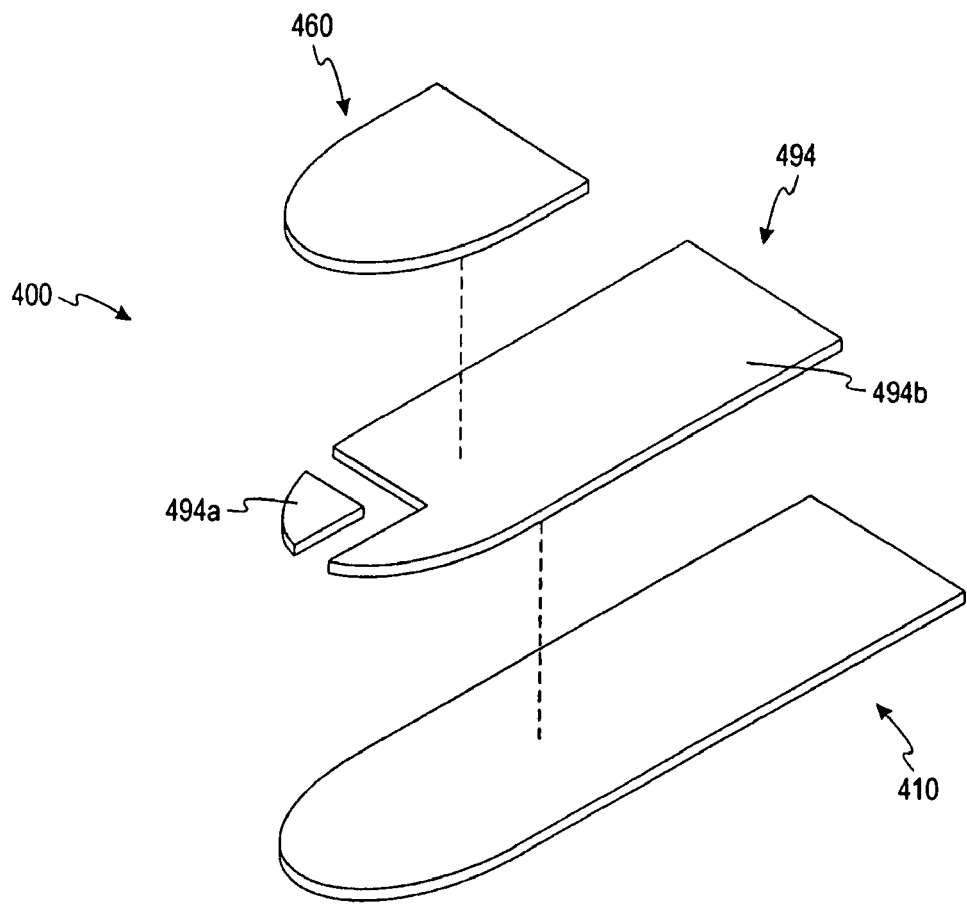
FIG. 13*a* is an exploded perspective view of an electrochemical test sensor according to a further embodiment.
Figure 13B:
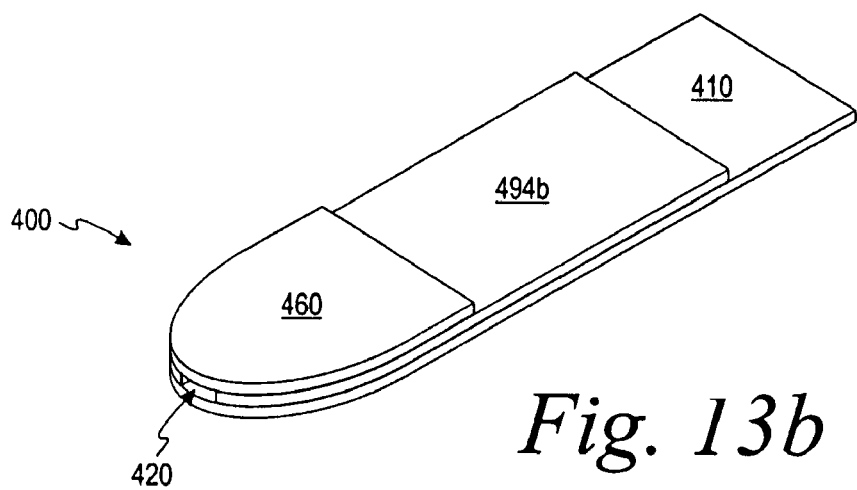
FIG. 13*b* is an assembled perspective view of the test sensor of FIG. 13*a*.

The spacers 494, 496 of FIGS. 11*b*, 11*c*, are adapted to be used in the base, lid and spacer combination as discussed above. As shown in FIG. 13*a*, 13*b*, an electrochemical test sensor 400 is similar to that shown in electrochemical test sensor 200 except that the electrochemical test sensor 400 includes exactly one side vent instead of opposing side vents.

The electrochemical test sensor includes a base 410, a lid 460 and a spacer 494. The base 410 and the lid 460 may be the same as the base 10 and the lid 60 discussed above. If spacer 496 is used instead of spacer 494, an electrochemical test sensor is formed that is similar to electrochemical test sensor 400 except that the vent is located on the opposing side.

It is contemplated that the test sensors may be other types of test sensors such as optical test sensors. Optical test sensor systems may use techniques such as, for example, transmission spectroscopy, diffuse reflectance or fluorescence spectroscopy for measuring the analyte concentration. An indicator reagent system and an analyte in a sample of body fluid are reacted to produce a chromatic reaction—the reaction between the reagent and analyte causes the sample to change color. The degree of color change is indicative of the analyte concentration in the body fluid. The color change of the sample is evaluated to measure the absorbance level of the transmitted light. Regular transmission spectroscopy is described in, for example, U.S. Pat. No. 5,866,349. Diffuse reflectance and fluorescence spectroscopy are described in, for example, U.S. Pat. No. 5,518,689 (entitled "Diffuse Light Reflectance Readhead"); U.S. Pat. No. 5,611,999 (entitled "Diffuse Light Reflectance Readhead"); and U.S. Pat. No. 5,194,393 (entitled "Optical Biosensor and Method of Use")

Figure 14A:
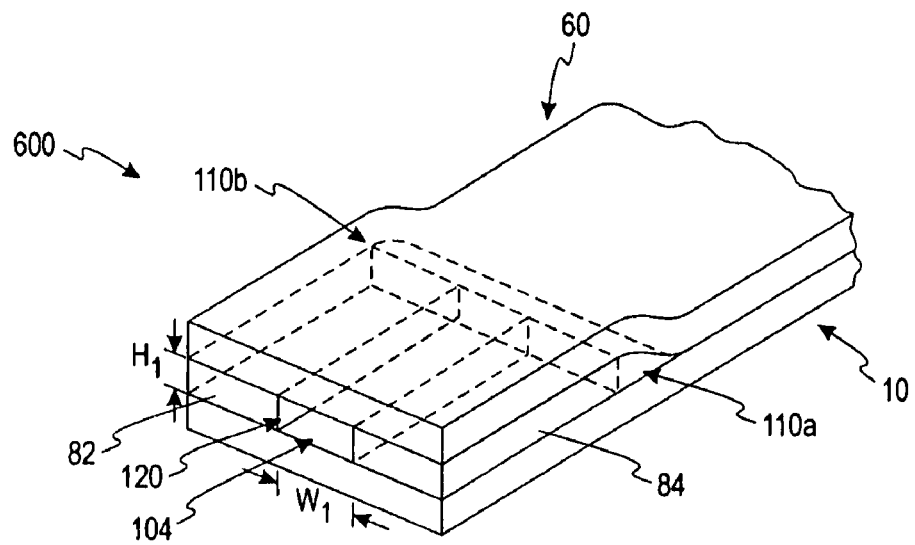
FIG. 14*a* is a partial perspective view of an optical test sensor according to one embodiment.
Figure 14B:
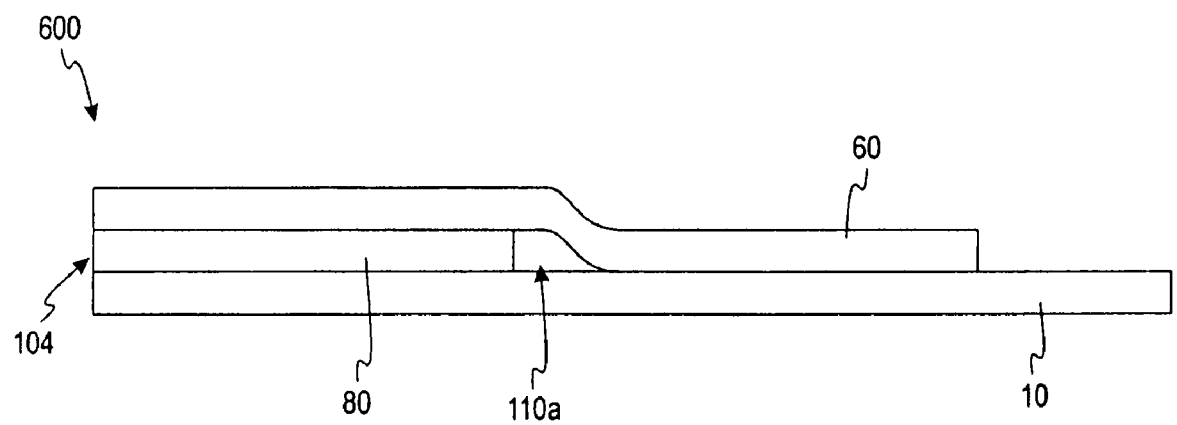
FIG. 14*b* is a side view of the optical test sensor of FIG. 14*a*.
Figure 15A:
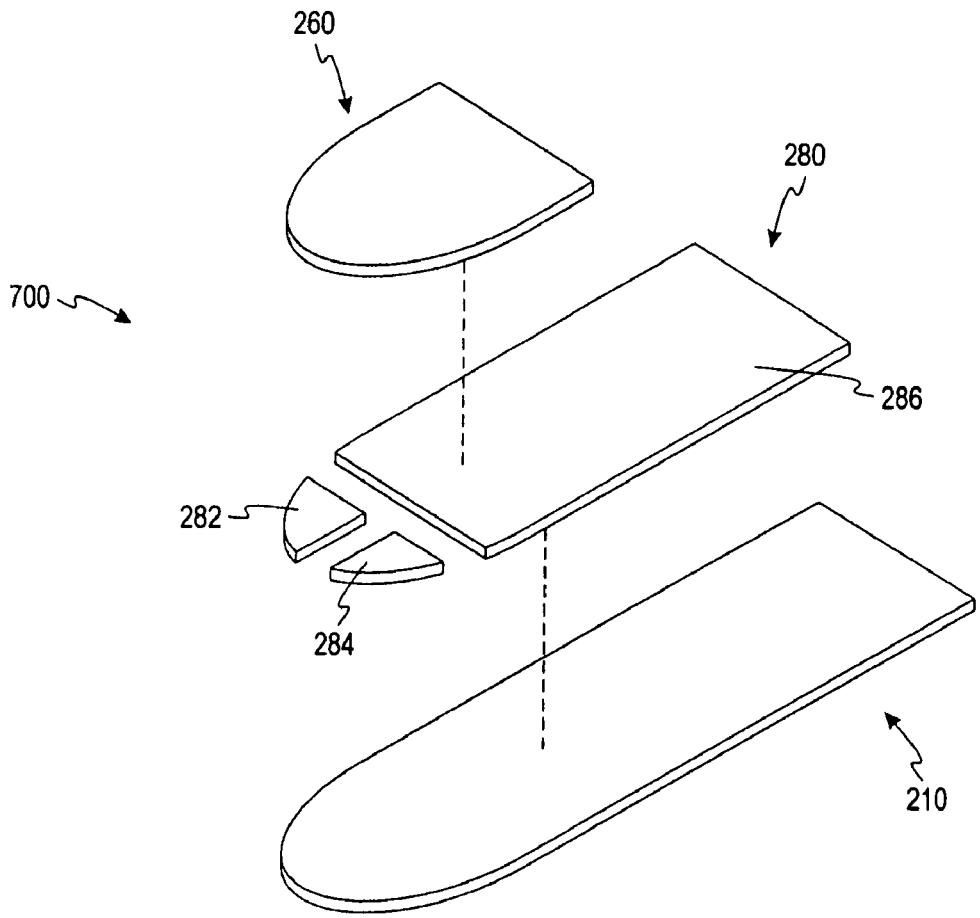
FIG. 15*a* is an exploded perspective view of an optical test sensor according to one embodiment.
Figure 15B:
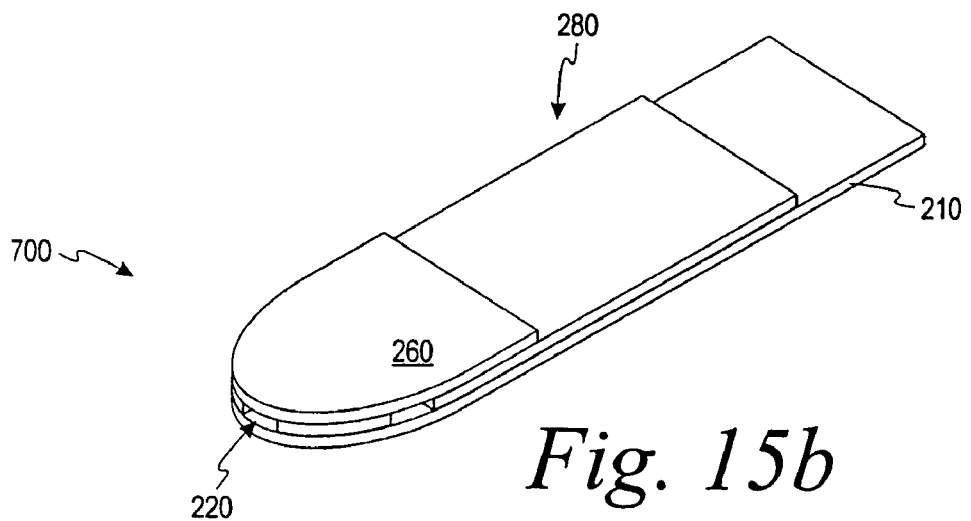
FIG. 15*b* is an assembled perspective view of the test sensor of FIG. 15*a*.
Figure 16A:
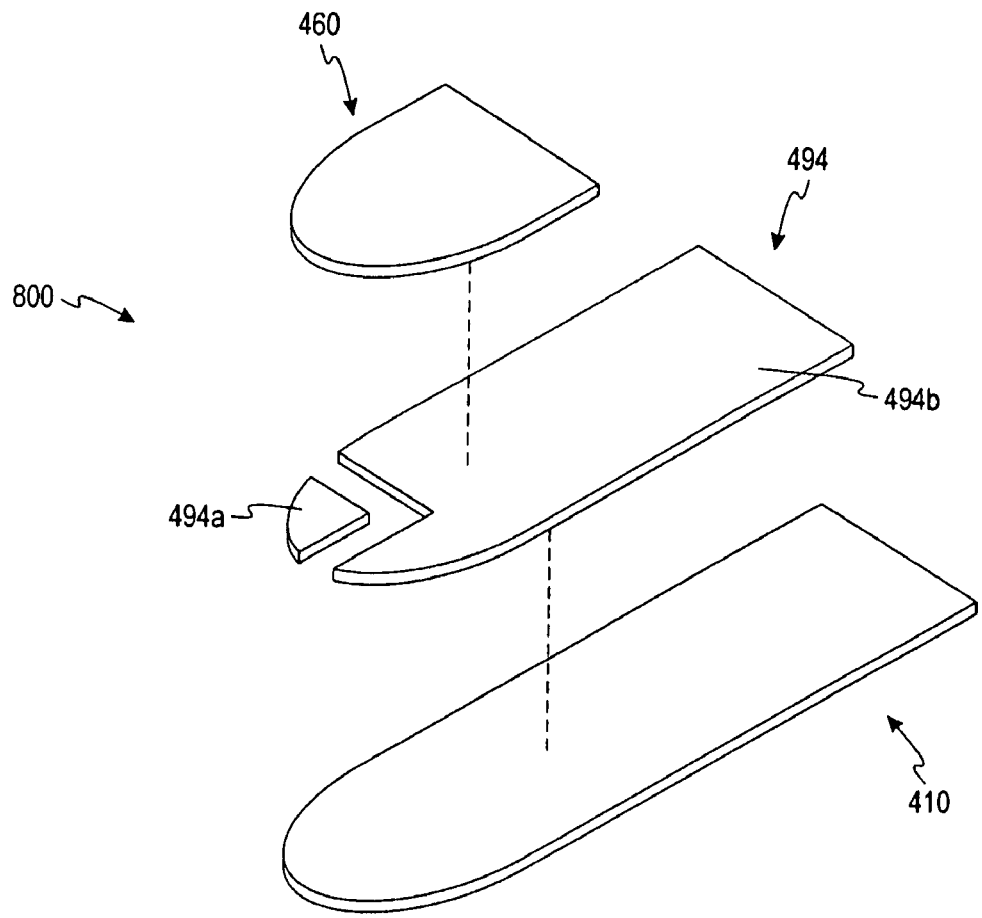
FIG. 16*a* is an exploded perspective view of an optical test sensor according to another embodiment.
Figure 16B:
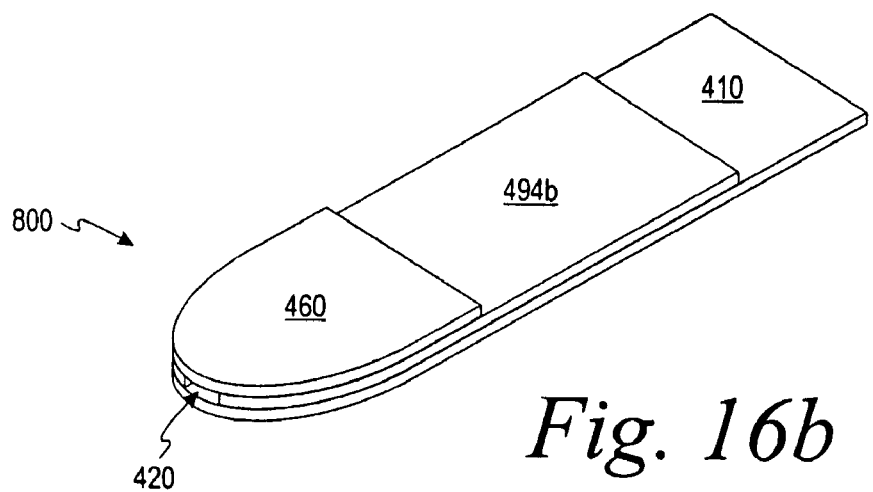
FIG. 16*b* is an assembled perspective view of the optical test sensor of FIG. 16*a*.

Examples of optical test sensors are shown in FIGS. 14-16. Specifically, FIGS. 14a, 14b shown a optical test sensor 600 that is similar to the test sensor 100 shown in FIGS. 4b, 4c. FIGS. 15a, 15b show an optical test sensor 700 that is similar to the test sensor 200. FIGS. 16a, 16b show an optical test sensor 800 that is similar to the test sensor 400.

Embodiment A

A test sensor adapted to assist in determining the concentration of an analyte in a fluid sample, the test sensor comprising:
a lid having an upper lid surface and a lower lid surface;
a base having an upper base surface and a lower base surface; and
a spacer having at least a first spacer section and a second spacer section, the first spacer section having a first spacer side and a first spacer end, the second spacer section having a second spacer side and a second spacer end,
wherein the lid, base and spacer are attached such that a fluid chamber is formed between a portion of the lower lid surface and the upper base surface, and between the first and second spacer sides,
wherein the lower lid surface, the upper base surface, the first spacer end and the second spacer end form at least one side vent therebetween, the at least one vent being in communication with the fluid chamber.

Embodiment B

The test sensor of embodiment A wherein the fluid chamber has a height of from about 3 to about 7 mils.

Embodiment C

The test sensor of embodiment B wherein the fluid chamber has a width of from about 3 to about 7 mils.

Embodiment D

The test sensor of embodiment A wherein the at least one side vent is exactly two side vents.

Embodiment E

The test sensor of embodiment A wherein the at least one side vent is exactly one side vent.

Embodiment F

The test sensor of embodiment A wherein the at least one side vent is generally parallel with the fluid chamber.

Embodiment G

The test sensor of embodiment A wherein the test sensor is an electrochemical test sensor and the base further includes a plurality of electrodes.

Embodiment H

The test sensor of embodiment A wherein the test sensor is an optical test sensor.

Embodiment I

The test sensor of embodiment A further including a first adhesive, the first adhesive being located between either the lid and the spacer or the base and the spacer.

Embodiment J

The test sensor of embodiment I further including a second adhesive, the second adhesive being located between the other one of the lid and the spacer and the base and the spacer.

Embodiment K

The test sensor of embodiment J wherein the first and second adhesives are the same.

Embodiment L

The test sensor of embodiment A wherein the base, lid and the spacer are made of a polymeric material.

Embodiment M

The test sensor of embodiment A wherein the spacer includes exactly a first spacer section and a second spacer section, the sections being distinct and separated from each other.

Embodiment N

The test sensor of embodiment A wherein the spacer includes exactly a first spacer section, a second spacer section and a third spacer section, the sections being distinct and separated from each other.

Embodiment O

The test sensor of embodiment A wherein the lower lid surface, the upper base surface, the first spacer end, the second spacer end and the third spacer end form two vents therebetween, the two side vents being in communication with the fluid chamber.

Process P

A method of determining an analyte concentration of a fluid sample using a meter, the method comprising the acts of:

providing a test sensor having a lid, a base and a spacer, the lid having an upper lid surface and a lower lid surface, the base having an upper base surface and a lower base surface, the spacer having at least a first spacer section and a second spacer section, the first spacer section having a first spacer side and a first spacer end, the second spacer section having a second spacer side and a second spacer end, the lower lid surface, upper base surface, the first spacer end and the second spacer end forming at least one side vent therebetween;

placing the fluid sample in the fluid chamber between the lower lid surface, the upper base surface, first spacer side, and the second spacer side, the fluid chamber being in communication with the at least one vent; and determining the analyte concentration of the sample using the test sensor and the meter.

Process Q

The method of process P wherein the fluid sample enters into the fluid chamber via capillary action.

Process R

The method of process P wherein the fluid sample is blood.

Process S

The method of process P wherein the analyte is glucose.

Process T

The method of process P wherein the fluid chamber has a height of from about 3 to about 7 mils.

Process U

The method of process T wherein the fluid chamber has a width of from about 3 to about 7 mils.

Process V

The method of process P wherein the at least one side vent is exactly two side vents.

Process W

The method of process P wherein the at least one side vent is exactly one side vent.

Process X

The method of process P wherein the at least one side vent is generally parallel with the fluid chamber.

Process Y

The method of process P wherein the test sensor is an electrochemical test sensor and the base further includes a plurality of electrodes.

Process Z

The method of process P wherein the test sensor is an optical test sensor.

Process AA

The method of process P wherein the test sensor further includes a first adhesive, the first adhesive being located between either the lid and the spacer or the base and the spacer.

Process BB

The method of process AA wherein the test sensor further includes a second adhesive, the second adhesive being located between the other one of the lid and the spacer and the base and the spacer.

Process CC

The method of process BB wherein the first and second adhesives are the same.

Process DD

The method of process P wherein the base, lid and the spacer are made of a polymeric material.

Process EE

The method of process P wherein the spacer includes exactly a first spacer section and a second spacer section, the sections being distinct and separated from each other.

Process FF

The method of process P wherein the spacer includes exactly a first spacer section, a second spacer section and a third spacer section, the sections being distinct and separated from each other.

Process GG

The method of process P wherein the lower lid surface, the upper base surface, the first spacer end, the second spacer end and the third spacer end form two vents therebetween, the two side vents being in communication with the fluid chamber.

Process HH

A method of forming a test sensor that is adapted to assist in determining an analyte concentration of a fluid sample, the method comprising the acts of:

providing a lid having an upper lid surface and a lower lid surface;

providing a base having an upper base surface and a lower base surface;

providing a spacer having at least a first spacer section and a second spacer section, the first spacer section having a first spacer side and a first spacer end, the second spacer section having a second spacer side and a second spacer end;

attaching the lid, base and the spacer such that a fluid chamber is formed between a portion of the lower lid surface and the upper base surface, and between the first and second spacer sides; and forming at least one side vent between the first spacer end, the second spacer end, the lower lid surface and the upper base surface, the at least one vent being in communication with the fluid chamber.

Process II

The method of process HH wherein the at least one side vent is formed with a reciprocating stepped platen.

Process JJ

The method of process HH wherein the at least one side vent is formed with a plurality of reciprocating platens.

Process KK

The method of process HH wherein the at least one side vent is exactly two side vents.

Process LL

The method of process HH wherein the at least one side vent is exactly one side vent.

Process MM

The method of process HH wherein the at least one side vent is generally parallel with the fluid chamber.

Process NN

The method of process HH wherein the test sensor is an electrochemical test sensor and the base further includes a plurality of electrodes.

Process OO

The method of process HH wherein the test sensor is an optical test sensor.

Process PP

The method of process HH wherein the attaching of the lid, base and spacer is via an adhesive.

Process QQ

The method of process HH wherein the spacer includes exactly a first spacer section and a second spacer section, the sections being distinct and separated from each other.

Process RR

The method of process HH wherein the spacer includes exactly a first spacer section, a second spacer section and a third spacer section, the sections being distinct and separated from each other.

Process SS

The method of process HH wherein the lower lid surface, the upper base surface, the first spacer end, the second spacer end and the third spacer end form two vents therebetween, the two side vents being in communication with the fluid chamber.

Process TT

The method of process HH wherein the lid, base and spacer are in the form of sheets.

Process UU

A method of forming a test sensor that is adapted to assist in determining an analyte concentration of a fluid sample, the method comprising the acts of:

providing a lid sheet having an upper lid surface and a lower lid surface;

providing a base sheet having an upper base surface and a lower base surface;

providing a spacer sheet having a first spacer section and a second spacer section, the first spacer section including a first spacer side and a first spacer end, the second spacer section including a second spacer side and a second spacer end;

removing material from the spacer sheet that will assist in forming at least one vent and a fluid chamber;

attaching the lid sheet, base sheet and the spacer sheet such that the fluid chamber and at least one vent are formed, the fluid chamber being formed between the lower lid surface, the upper base surface, the first spacer side and the second spacer side, the at least one vent being formed between the first spacer end, the second spacer end, the lower lid surface and the upper base surface, the at least one vent being in communication with the fluid chamber; and forming a plurality of test sensors from the attached lid sheet, base sheet and spacer sheet.

Process VV

The method of process UU wherein the removing material from the spacer sheet is performed by punching material from the spacer sheet.

Process WW

The method of process UU wherein the removing of material from the spacer sheet is performed by cutting material from the spacer sheet.

Process XX

The method of process UU wherein the forming of the test sensors is performed by punching material from the attached base, lid and spacer sheets.

Process YY

The method of process UU wherein the forming of the test sensors is performed by cutting material from the attached base, lid and spacer sheets.

Process ZZ

The method of process UU wherein the at least one side vent is exactly one side vent.

Process AAA

The method of process UU wherein the at least one side vent is generally parallel with the fluid chamber.

Process BBB

The method of process UU wherein the test sensor is an electrochemical test sensor and the base further includes a plurality of electrodes.

Process CCC

The method of process UU wherein the test sensor is an optical test sensor.

Process DDD

The method of process UU wherein the attaching of the lid, base and spacer is via an adhesive.

Process EEE

The method of process UU wherein the spacer includes exactly a first spacer section and a second spacer section, the sections being distinct and separated from each other.

Process FFF

The method of process UU wherein the spacer includes exactly a first spacer section, a second spacer section and a third spacer section, the sections being distinct and separated from each other.

Process GGG

The method of process UU wherein the lower lid surface, the upper base surface, the first spacer end, the second spacer end and the third spacer end form two vents therebetween, the two side vents being in communication with the fluid chamber.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

What is claimed is:

1. A test sensor adapted to assist in determining the concentration of an analyte in a fluid sample, the test sensor comprising:
    a lid having an upper lid surface and a lower lid surface;
    a base having an upper base surface and a lower base surface; and
    a spacer having at least a first spacer section and a second spacer section, the first spacer section having a first spacer side and a first spacer end, the second spacer section having a second spacer side and a second spacer end,
    wherein the lid, base and spacer are attached such that a fluid chamber is formed between a portion of the lower lid surface and the upper base surface, and between the first and second spacer sides,
    wherein the lower lid surface, the upper base surface, the first spacer end and the second spacer end form at least one side vent therebetween, the at least one side vent being in communication with the fluid chamber, the at least one side vent being generally perpendicular to the fluid chamber, the at least one side vent being in generally the same plane as the fluid sample flow in the fluid chamber.

2. The test sensor of claim 1, wherein the fluid chamber has a height of from about 3 to about 7 mils.

3. The test sensor of claim 2, wherein the fluid chamber has a width of from about 3 to about 7 mils.

4. The test sensor of claim 1, wherein the at least one side vent is exactly two side vents.

5. The test sensor of claim 1, wherein the at least one side vent is exactly one side vent.

6. The test sensor of claim 1, wherein the test sensor is an electrochemical test sensor and the base further includes a plurality of electrodes.

7. The test sensor of claim 1, wherein the test sensor is an optical test sensor.

8. The test sensor of claim 1, wherein the spacer includes exactly a first spacer section and a second spacer section, the sections being distinct and separated from each other.

9. The method of claim 1, wherein the lid and base are formed in the absence of an aperture.

10. A test sensor adapted to assist in determining the concentration of an analyte in a fluid sample, the test sensor comprising:
    a lid having an upper lid surface and a lower lid surface;
    a base having an upper base surface and a lower base surface; and
    a spacer having at least a first spacer section and a second spacer section, the first spacer section having a first spacer side and a first spacer end, the second spacer section having a second spacer side and a second spacer end,
    wherein the lid, base and spacer are attached such that a fluid chamber is formed between a portion of the lower lid surface and the upper base surface, and between the first and second spacer sides,
    wherein the lower lid surface, the upper base surface, the first spacer end and the second spacer end form at least one side vent therebetween, the at least one vent being in communication with the fluid chamber,
    wherein the spacer includes exactly a first spacer section, a second spacer section and a third spacer section, the sections being distinct and separated from each other.

11. The test sensor of claim 10, wherein the lower lid surface, the upper base surface, the first spacer end, the second spacer end and the third spacer end form two vents therebetween, the two side vents being in communication with the fluid chamber.

12. A method of determining an analyte concentration of a fluid sample using a meter, the method comprising the acts of:
    providing a test sensor having a lid, a base and a spacer, the lid having an upper lid surface and a lower lid surface, the base having an upper base surface and a lower base surface, the spacer having at least a first spacer section and a second spacer section, the first spacer section having a first spacer side and a first spacer end, the second spacer section having a second spacer side and a second spacer end, the lower lid surface, upper base surface, the first spacer end and the second spacer end forming at least one side vent therebetween;
    placing the fluid sample in the fluid chamber between the lower lid surface, the upper base surface, first spacer side, and the second spacer side, the fluid chamber being in communication with the at least one side vent, the at least one side vent being generally perpendicular to the fluid chamber, the at least one side vent being in generally the same plane as the fluid sample flow in the fluid chamber; and
    determining the analyte concentration of the sample using the test sensor and the meter.

13. The method of claim 12, wherein the fluid sample enters into the fluid chamber via capillary action.

14. The method of claim 12, wherein the fluid sample is blood.

15. The method of claim 12, wherein the analyte is glucose.

16. The method of claim 12, wherein the at least one side vent is exactly two side vents.

17. The method of claim 12, wherein the at least one side vent is exactly one side vent.

18. The method of claim 12, wherein the spacer includes exactly a first spacer section, a second spacer section and a third spacer section, the sections being distinct and separated from each other.

19. The method of claim 12, wherein the lid and base are formed in the absence of an aperture.

20. A method of forming a test sensor that is adapted to assist in determining an analyte concentration of a fluid sample, the method comprising the acts of:
providing a lid having an upper lid surface and a lower lid surface;
providing a base having an upper base surface and a lower base surface;
providing a spacer having at least a first spacer section and a second spacer section, the first spacer section having a first spacer side and a first spacer end, the second spacer section having a second spacer side and a second spacer end;
attaching the lid, base and the spacer such that a fluid chamber is formed between a portion of the lower lid surface and the upper base surface, and between the first and second spacer sides; and
forming at least one side vent between the first spacer end, the second spacer end, the lower lid surface and the upper base surface, the at least one side vent being in communication with the fluid chamber, the at least one side vent being generally perpendicular to the fluid chamber, the at least one side vent being in generally the same plane as the fluid sample flow in the fluid chamber.

21. The method of claim 20, wherein the at least one side vent is formed with a reciprocating stepped platen.

22. The method of claim 20, wherein the at least one side vent is formed with a plurality of reciprocating platens.

23. The method of claim 20, wherein the at least one side vent is exactly two side vents.

24. The method of claim 20, wherein the at least one side vent is exactly one side vent.

25. The method of claim 20, wherein the spacer includes exactly a first spacer section, a second spacer section and a third spacer section, the sections being distinct and separated from each other.

26. The method of claim 20, wherein the lid and base are formed in the absence of an aperture.

27. A method of forming a test sensor that is adapted to assist in determining an analyte concentration of a fluid sample, the method comprising the acts of:
providing a lid sheet having an upper lid surface and a lower lid surface;
providing a base sheet having an upper base surface and a lower base surface;
providing a spacer sheet having a first spacer section and a second spacer section, the first spacer section including a first spacer side and a first spacer end, the second spacer section including a second spacer side and a second spacer end;
removing material from the spacer sheet that will assist in forming at least one vent and a fluid chamber;
attaching the lid sheet, base sheet and the spacer sheet such that the fluid chamber and at least one vent are formed, the fluid chamber being formed between the lower lid surface, the upper base surface, the first spacer side and the second spacer side, the at least one vent being formed between the first spacer end, the second spacer end, the lower lid surface and the upper base surface, the at least one side vent being in communication with the fluid chamber, the at least one side vent being generally perpendicular to the fluid chamber, the at least one side vent being in generally the same plane as the fluid sample flow in the fluid chamber; and
forming a plurality of test sensors from the attached lid sheet, base sheet and spacer sheet.

28. The method of claim 27, wherein the removing material from the spacer sheet is performed by punching material from the spacer sheet.

29. The method of claim 27, wherein the removing of material from the spacer sheet is performed by cutting material from the spacer sheet.

30. The method of claim 27, wherein the forming of the test sensors is performed by punching material from the attached base, lid and spacer sheets.

31. The method of claim 27, wherein the forming of the test sensors is performed by cutting material from the attached base, lid and spacer sheets.

32. A test sensor adapted to assist in determining the concentration of an analyte in a fluid sample, the test sensor comprising:
a lid having an upper lid surface and a lower lid surface;
a base having an upper base surface and a lower base surface; and
a spacer having at least a first spacer section and a second spacer section, the first spacer section having a first spacer side and a first spacer end, the second spacer section having a second spacer side and a second spacer end,
wherein the lid, base and spacer are attached such that a fluid chamber is formed between a portion of the lower lid surface and the upper base surface, and between the first and second spacer sides, the fluid chamber being substantially the same length as at least one of the first and second spacer sides,
wherein the lower lid surface, the upper base surface, the first spacer end and the second spacer end form at least one side vent therebetween, the at least one side vent being in communication with the fluid chamber, the at least one side vent being generally perpendicular to the fluid chamber.

33. A method of determining an analyte concentration of a fluid sample using a meter, the method comprising the acts of:
providing a test sensor having a lid, a base and a spacer, the lid having an upper lid surface and a lower lid surface, the base having an upper base surface and a lower base surface, the spacer having at least a first spacer section and a second spacer section, the first spacer section having a first spacer side and a first spacer end, the second spacer section having a second spacer side and a second spacer end, the lower lid surface, upper base surface, the first spacer end and the second spacer end forming at least one side vent therebetween;
placing the fluid sample in the fluid chamber between the lower lid surface, the upper base surface, first spacer side, and the second spacer side, the fluid chamber being in communication with the at least one side vent, the at least one side vent being generally perpendicular to the fluid chamber, the fluid chamber being substantially the same length as the first and second spacer sides; and
determining the analyte concentration of the sample using the test sensor and the meter.

34. A test sensor adapted to assist in determining the concentration of an analyte in a fluid sample, the test sensor comprising:

a lid having an upper lid surface and a lower lid surface;

a base having an upper base surface and a lower base surface; and a spacer having at least a first spacer section and a second spacer section, the first spacer section having a first spacer side and a first spacer end, the second spacer section having a second spacer side and a second spacer end, wherein the lid, base and spacer are attached such that a fluid chamber is formed between a portion of the lower lid surface and the upper base surface, and between the first and second spacer sides, wherein the lower lid surface, the upper base surface, the first spacer end and the second spacer end form at least one side vent therebetween, the at least one side vent being in communication with the fluid chamber, the at least one side vent being in generally the same plane as the fluid sample flow in the fluid chamber, the at least one side vent bisecting the fluid chamber such that the at least one side vent and the fluid chamber are not aligned with each other.

* * * * *